(12) United States Patent
Lacoma

(10) Patent No.: US 12,691,005 B2
(45) Date of Patent: Jul. 28, 2026

(54) FACE MASKS WITH NOISE ATTENUATION

(71) Applicant: SharkNinja Operating LLC,
Needham, MA (US)

(72) Inventor: Max Lacoma, Huntington, NY (US)

(73) Assignee: SharkNinja Operating LLC,
Needham, MA (US)

( * ) Notice: Subject to any disclaimer, the term of this
patent is extended or adjusted under 35
U.S.C. 154(b) by 253 days.

(21) Appl. No.: 18/411,644

(22) Filed: Jan. 12, 2024

(65) Prior Publication Data

US 2025/0228703 A1 Jul. 17, 2025

(51) Int. Cl.
 *A61F 7/02* (2006.01)
 *A61F 7/00* (2006.01)
 *F25B 21/04* (2006.01)
(52) U.S. Cl.
 CPC ............... *A61F 7/02* (2013.01); *F25B 21/04*
 (2013.01); *A61F 2007/0003* (2013.01); *A61F*
 *2007/0075* (2013.01); *A61F 2007/0225*
 (2013.01)
(58) Field of Classification Search
 CPC .......... A61F 2007/0075; A45D 44/002; A61N
 5/0616
 See application file for complete search history.

(56) References Cited

U.S. PATENT DOCUMENTS

| | | |
|---|---|---|
| 7,159,273 B2 | 1/2007 | Fawcett |
| 7,353,908 B1 | 4/2008 | French |
| 7,523,750 B2 | 4/2009 | Krzysztofik |
| 7,546,898 B2 | 6/2009 | Tracy et al. |
| 7,724,515 B2 | 5/2010 | Fukuda et al. |
| 7,824,394 B2 | 11/2010 | Manstein |
| 7,969,733 B1 | 6/2011 | Abbay et al. |
| 8,155,332 B2 | 4/2012 | Gross et al. |
| 8,236,038 B2 | 8/2012 | Nofzinger |
| 8,585,688 B2 | 11/2013 | Zemmouri et al. |
| 8,714,302 B2 | 5/2014 | Gradinger et al. |

(Continued)

FOREIGN PATENT DOCUMENTS

| | | |
|---|---|---|
| CA | 3024493 A1 | 11/2017 |
| CN | 101159133 B | 1/2012 |

(Continued)

OTHER PUBLICATIONS

Foreign Reference and Machine Translation of WO 2020145448
(Year: 2020).*

(Continued)

*Primary Examiner* — Kaitlyn E Smith
(74) *Attorney, Agent, or Firm* — Mintz, Levin, Cohn,
Ferris, Glovsky and Popeo, P.C. US

(57) ABSTRACT

Various illustrative systems, devices, and methods for face
masks are provided. In general, a face mask is configured to
provide cooling therapy to a user wearing the face mask. In
an exemplary implementation, the face mask includes a
thermoelectric cooling device, such as a Peltier device, a
thermoelectric cooler (TEC), or other thermoelectric cooling
device. The face mask includes a fan configured to blow air
configured to dissipate the heat created by the thermoelectric
cooling device. The face mask includes a noise attenuation
system configured to attenuate the generated noise that is
radiated into the environment, and thus, heard by the user
due to use of the fan.

19 Claims, 11 Drawing Sheets

(56) References Cited

U.S. PATENT DOCUMENTS

| | | | |
|---|---|---|---|
| 8,734,434 B2 | 5/2014 | Hansen et al. | |
| 8,758,101 B2 | 6/2014 | Khalitov et al. | |
| 8,858,583 B2 | 10/2014 | Shtram et al. | |
| 9,084,665 B2 | 7/2015 | Beardall et al. | |
| 9,492,313 B2 | 11/2016 | Nofzinger | |
| 9,532,832 B2 | 1/2017 | Ron Edoute et al. | |
| 9,579,507 B2 | 2/2017 | Cakmak | |
| 9,797,412 B2 | 10/2017 | Le Roy et al. | |
| 9,872,104 B2 | 1/2018 | Hopkins | |
| 10,213,334 B2 | 2/2019 | Nofzinger et al. | |
| 10,292,859 B2 | 5/2019 | Levinson et al. | |
| 10,299,525 B1 | 5/2019 | Buckman | |
| 10,388,327 B2 | 8/2019 | Eguchi et al. | |
| 10,495,094 B2 | 12/2019 | Hopkins | |
| 10,512,319 B2 | 12/2019 | Yamazaki | |
| 10,565,974 B1 | 2/2020 | Bhatia et al. | |
| 10,575,683 B2 | 3/2020 | Nernberger et al. | |
| 10,610,001 B2 | 4/2020 | Kim | |
| 10,610,661 B2 | 4/2020 | Nofzinger | |
| 10,624,500 B2 | 4/2020 | Diaz et al. | |
| 10,765,885 B2 | 9/2020 | Schanze | |
| 10,864,348 B2 | 12/2020 | Walker et al. | |
| 11,019,859 B1 | 6/2021 | Rothenberg | |
| 11,020,607 B2 | 6/2021 | Song | |
| 11,259,627 B2 | 3/2022 | Boersma et al. | |
| 11,504,159 B2 | 11/2022 | Scooros | |
| 11,517,639 B2 | 12/2022 | Yildirim et al. | |
| 11,540,610 B2 | 1/2023 | Park et al. | |
| 11,642,546 B2 | 5/2023 | Dai | |
| 11,668,328 B2 | 6/2023 | Ji et al. | |
| 11,684,510 B2 | 6/2023 | Nofzinger | |
| 11,713,904 B2 | 8/2023 | Eichelberger et al. | |
| 11,725,846 B2 | 8/2023 | Pandit et al. | |
| 11,801,160 B2 | 10/2023 | Schöggler | |
| 2005/0039809 A1 | 2/2005 | Speldrich | |
| 2015/0176860 A1* | 6/2015 | Hattan | A61F 7/0085 181/224 |
| 2015/0238725 A1 | 8/2015 | Tucker et al. | |
| 2017/0252534 A1 | 9/2017 | Nofzinger | |
| 2017/0306984 A1* | 10/2017 | Peterson | F04D 25/08 |
| 2019/0083688 A1* | 3/2019 | Sutton | A61M 1/815 |
| 2019/0336215 A1 | 11/2019 | Mescher et al. | |
| 2020/0046936 A1 | 2/2020 | Nofzinger et al. | |
| 2020/0229530 A1 | 7/2020 | Feher | |
| 2022/0000199 A1 | 1/2022 | Dickinson et al. | |
| 2022/0080221 A1 | 3/2022 | Gross | |
| 2022/0212028 A1 | 7/2022 | Lee | |
| 2022/0219010 A1 | 7/2022 | Kim | |
| 2022/0273088 A1 | 9/2022 | Goo | |
| 2022/0280748 A1 | 9/2022 | Tucker et al. | |
| 2023/0025019 A1 | 1/2023 | Youngblood et al. | |
| 2023/0050908 A1 | 2/2023 | Nofzinger | |
| 2023/0068774 A1 | 3/2023 | Smith | |
| 2023/0165752 A1 | 6/2023 | Woo | |

FOREIGN PATENT DOCUMENTS

| | | | | |
|---|---|---|---|---|
| CN | 103861214 B | 4/2016 | | |
| CN | 106955426 A | 7/2017 | | |
| CN | 107149725 A | 9/2017 | | |
| CN | 107469237 A | 12/2017 | | |
| CN | 109045482 A | 12/2018 | | |
| CN | 106402974 B | 2/2019 | | |
| CN | 107044449 B | 3/2019 | | |
| CN | 107320853 B | 3/2019 | | |
| CN | 106377846 B | 6/2019 | | |
| CN | 110917507 A | 3/2020 | | |
| CN | 105736480 B | 6/2020 | | |
| CN | 108475516 B | 6/2020 | | |
| CN | 108759062 B | 9/2020 | | |
| CN | 111790058 A | 10/2020 | | |
| CN | 108309093 B | 1/2021 | | |
| CN | 112494806 A | 3/2021 | | |
| CN | 111603678 B | 10/2021 | | |
| CN | 112205848 B | 11/2021 | | |
| CN | 109730551 B | 3/2022 | | |
| CN | 113995964 B | 3/2022 | | |
| CN | 114377299 A | 4/2022 | | |
| CN | 115253086 A | 11/2022 | | |
| CN | 115957446 A | 4/2023 | | |
| CN | 116236702 A | 6/2023 | | |
| CN | 116392724 A | 7/2023 | | |
| CN | 114028728 B | 8/2023 | | |
| CN | 115040788 B | 8/2023 | | |
| DE | 202023105632 U1 | 10/2023 | | |
| EP | 2392375 A2 | 12/2011 | | |
| EP | 1621752 B1 | 5/2013 | | |
| EP | 2910276 B1 | 6/2021 | | |
| KR | 20210010715 A | * 1/2021 | | A61F 7/007 |
| WO | 2014078630 A1 | 5/2014 | | |
| WO | 2015013576 A1 | 1/2015 | | |
| WO | 2017201088 A1 | 11/2017 | | |
| WO | WO-2020145448 A1 | * 7/2020 | | A61F 7/02 |
| WO | 2022045850 A1 | 3/2022 | | |
| WO | 2022248793 A1 | 12/2022 | | |
| WO | 2023031619 A3 | 3/2023 | | |

OTHER PUBLICATIONS

Foreign Reference and Machine Translation of KR 20210010715 (Year: 2021).*

International Search Report and Written Opinion received for PCT Patent Application No. PCT/US2024/059539 mailed on Mar. 14, 2025, 16 pages.

* cited by examiner

231

208

240b

240

240a

240c

228

226

FACE MASKS WITH NOISE ATTENUATION

FIELD

The present disclosure generally relates to face masks with noise attenuation.

BACKGROUND

Cooling can be applied to skin on a user's face for various health and/or aesthetic reasons. Face masks worn by a user may be used to apply the cooling. Some face masks include a Peltier cooler to generate the cooling delivered to the user's face. However, Peltier coolers also generate heat. The heat can interfere adversely with the cooling effect provided by the face mask. Accordingly, there remains a need for improved devices, systems, and methods for face masks.

SUMMARY

In general, systems, devices, and methods for face masks are provided.

In one aspect, an apparatus with noise attenuation is provided that in one implementation includes a face mask configured to be worn on a face of a user. The face mask includes a first air inlet through which air external to the face mask is configured to enter a first flow path, an air outlet through which the air is configured to exit the first flow path to exit the face mask, a first thermoelectric cooling device configured to generate cooling and to generate heat, a first fan configured to cause air to enter the face mask through the first air inlet and to flow along the first flow path from the first air inlet to the first fan and from the first fan along the first flow path to the air outlet, and at least one of: a first flared acoustic waveguide at the first air inlet, a first acoustic chamber along the first flow path and located between the first air inlet and the first fan, and a first tortuous path along the first flow path and located between the first fan and the air outlet. The cooling is configured to be applied to the face of the user with user wearing the face mask. The air flowing along the first flow path is configured to dissipate the heat.

The apparatus can vary in any number of ways. For example, the face mask can includes at least the first acoustic chamber; the first acoustic chamber can include a first chamber, a second chamber, and a third chamber; air can be configured to flow from the first air inlet to the first chamber, from the first chamber to the second chamber, and from the second chamber to the third chamber; and the second chamber can be expanded as compared to the first and third chambers.

For another example, the face mask can include at least the first tortuous path, and the first tortuous path can define a plurality of twists and turns along the first flow path.

For yet another example, the face mask can include at least the first flared acoustic waveguide, and the first flared acoustic waveguide can be located at an interface between the first air flow path and the first air inlet.

For still another example, wherein the first air inlet and the air outlet can be located at a bottom of face mask.

For another example, the face mask can further include a first heat sink facing the first thermoelectric cooling device and located downstream of the first fan such that the first fan is configured to blow air toward the first heat sink.

For yet another example, the face mask can further include a second flared acoustic waveguide at the air outlet.

For another example, the face mask can include at least two of the first flared acoustic waveguide, the first acoustic chamber, and the first tortuous path.

For yet another example, the face mask can include all of the first flared acoustic waveguide, the first acoustic chamber, and the first tortuous path.

For another example, the face mask can further include a second air inlet through which air external to the face mask is configured to enter a second flow path, a second thermoelectric cooling device configured to generate cooling and to generate heat, a second fan configured to cause air to enter the face mask through the second air inlet and to flow along the second flow path from the second air inlet to the second fan and from the second fan along the second flow path to the air outlet, and at least one of: a second flared acoustic waveguide at the second air inlet, a second acoustic chamber along the second flow path and located between the second air inlet and the second fan, and a second tortuous path along the second flow path and located between the second fan and the air outlet; the cooling generated by the second thermoelectric cooling device can be configured to be applied to the face of the user with user wearing the face mask; and the air flowing along the second flow path can be configured to dissipate the heat generated by the second thermoelectric cooling device. Further, the face mask can include at least the first acoustic chamber and the second acoustic chamber, the first acoustic chamber can mirror the second acoustic chamber, the first acoustic chamber can includes a first chamber, a second chamber, and a third chamber, the second acoustic chamber can include a fourth chamber, a fifth chamber, and a sixth chamber, air can be configured to flow from the first air inlet to the first chamber, from the first chamber to the second chamber, and from the second chamber to the third chamber, the second chamber can be expanded as compared to the first and third chambers, air can be configured to flow from the second air inlet to the fourth chamber, from the fourth chamber to the fifth chamber, and from the fifth chamber to the sixth chamber, and the fifth chamber can be expanded as compared to the fourth and sixth chambers; the face mask can include at least the first tortuous path and the second tortuous path, the first tortuous path can mirror the second tortuous path, the first tortuous path can define a first plurality of twists and turns along the first flow path, and the second tortuous path can define a second plurality of twists and turns along the second flow path; the face mask can include at least the first flared acoustic waveguide and the second flared acoustic waveguide, the first flared acoustic waveguide can be located at an interface between the first air flow path and the first air inlet, and the second flared acoustic waveguide can be located at an interface between the second air flow path and the second air inlet; the first air inlet, the second air inlet, and the air outlet can be located at a bottom of the face mask; the air outlet can be one of: a shared outlet through which air is configured to exit each of the first and second air flow paths, and first and second air outlets, air being configured to flow through the first air outlet from the first air flow path and through the second air outlet from the second air flow path; the face mask can further include a first heat sink facing the first thermoelectric cooling device and located downstream of the first fan such that the first fan is configured to blow air toward the first heat sink, and a second heat sink facing the second thermoelectric cooling device and located downstream of the second fan such that the second fan is configured to blow air toward the second heat sink; the face mask can include at least two of the first flared acoustic waveguide, the first acoustic chamber, and the first tortuous path; and/or the face mask can include at least two of the second flared acoustic waveguide, the second acoustic chamber, and the second tortuous path. Further, the face mask can include all of the first flared acoustic waveguide, the first acoustic chamber, and the first tortuous path, and the face mask can include all of the second flared acoustic waveguide, the second acoustic chamber, and the second tortuous path.

In another implementation, an apparatus with noise attenuation includes a face mask configured to be worn on a face of a user. The face mask includes a first thermoelectric cooling device configured to generate cooling and to generate heat. The cooling generated by the first thermoelectric cooling device is configured to be applied to the face of the user with the user wearing the face mask. The face mask also includes a first fan configured to cause a first air flow configured to dissipate the heat generated by the first thermoelectric cooling device, a first noise attenuation system configured to attenuate noise caused by the first fan, and a second thermoelectric cooling device configured to generate cooling and to generate heat. The cooling generated by the second thermoelectric cooling device is configured to be applied to the face of the user with the user wearing the face mask. The face mask also includes a second fan configured to cause a second air flow configured to dissipate the heat generated by the second thermoelectric cooling device, and a second noise attenuation system configured to attenuate noise caused by the second fan.

The apparatus can have any number of variations. For example, the first noise attenuation system can include at least one of a first flared acoustic waveguide, a first acoustic chamber, and a first tortuous path, and the second noise attenuation system can include at least one of a second flared acoustic waveguide, a second acoustic chamber, and a second tortuous path.

For another example, the first noise attenuation system can include at least two of a first flared acoustic waveguide, a first acoustic chamber, and a first tortuous path, and the second noise attenuation system can include at least two of a second flared acoustic waveguide, a second acoustic chamber, and a second tortuous path.

For yet another example, the first noise attenuation system can include a first flared acoustic waveguide, a first acoustic chamber, and a first tortuous path, and the second noise attenuation system can include a second flared acoustic waveguide, a second acoustic chamber, and a second tortuous path.

In another aspect, a method is provided that in one implementation includes running a first fan of a face mask worn on a face of a user, and attenuating noise caused by the running of the fan using a first noise attenuation system of the face mask.

The method can vary in any number of ways. For example, the face mask can include any one or more features of the apparatuses with noise attenuation described above.

BRIEF DESCRIPTION OF DRAWINGS

This disclosure will be more fully understood from the following detailed description taken in conjunction with the accompanying drawings, in which.

DETAILED DESCRIPTION

Figure 1:
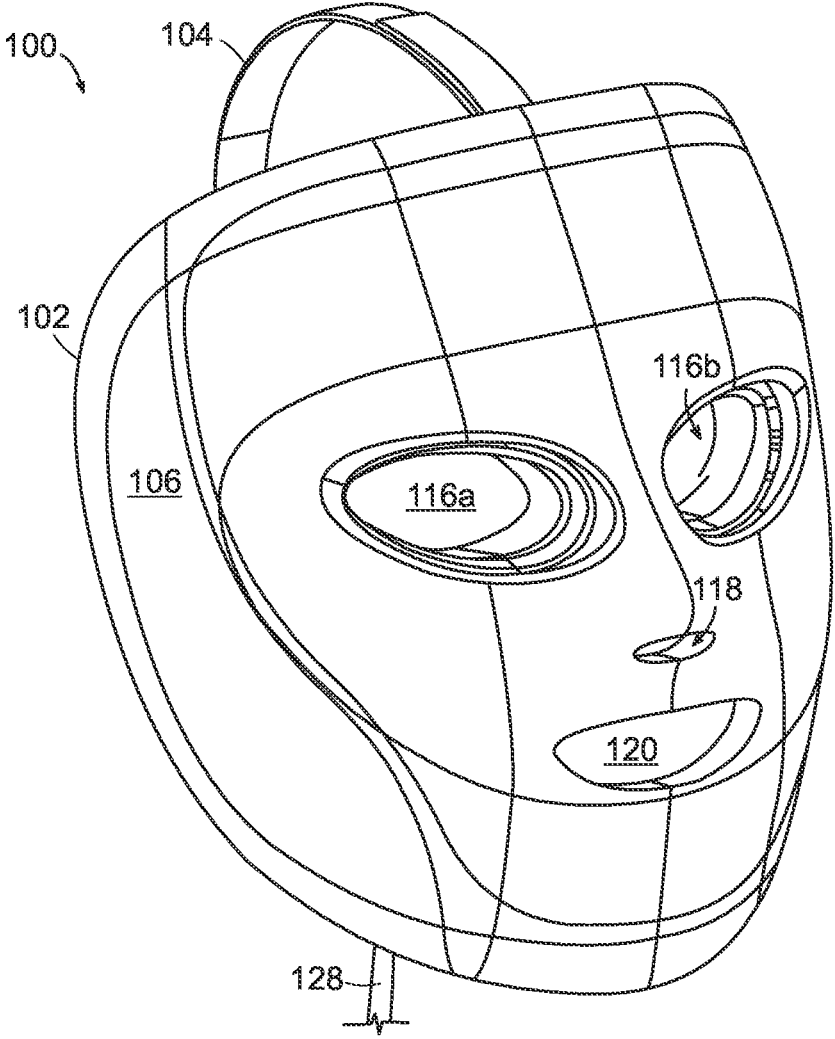
FIG. 1 is a perspective view of one implementation of a face mask.

Certain embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape.

Various illustrative systems, devices, and methods for face masks are provided. In general, a face mask is configured to provide cooling therapy to a user wearing the face mask. In an exemplary implementation, the face mask includes a thermoelectric cooling device, such as a Peltier device, a thermoelectric cooler (TEC), or other thermoelectric cooling device. The thermoelectric cooling device is configured to generate heat through a thermoelectric effect where a heat flux is created at a junction of two different types of materials. The heat flux creates a cold area and a hot area. The cold area is configured to face toward the user's face to provide cool energy to the user's skin. The hot area creates heat energy that the face mask is configured to dissipate to help prevent the heat from interfering adversely with the cooling provided to the user by the face mask. Dissipating the heat generated from the thermoelectric cooling device may help prevent the heat from interfering adversely with the cooling effect provided by the face mask.

The face mask includes a fan configured to blow air configured to dissipate the heat created by the thermoelectric cooling device. However, using the fan creates noise that can irritate the user wearing the face mask and thus degrade user experience, particularly since the face mask is located near the user's ears. The face mask includes a noise attenuation system configured to attenuate the generated noise that is radiated into the environment, and thus, heard by the user due to use of the fan. The noise attenuation system is configured to automatically attenuate noise, so the user does not need to take any particular action specific to reducing noise. Noise heard by the user may thus be automatically reduced whenever the face mask is on the user's face and the fan is running, thereby improving user experience. In implementations where the face mask includes more than one fan, the face mask can include multiple noise attenuations systems, one per fan, so noise generated by all the fans can be attenuated.

In an exemplary implementation, the noise attenuation system includes an acoustic chamber upstream of the fan and a tortuous air path downstream of the fan. The acoustic chamber is located adjacent an air inlet through which air enters the face mask, e.g., under force provided by the fan, and is located along an air inflow path along which the air flows from the air inlet to the fan. The acoustic chamber has dimensions tuned to maximize noise reduction in a desired frequency band, e.g., a frequency band sensitive to human hearing. The air entering the air inlet and flowing along the air inflow path causes noise that would be easily heard by the user without the acoustic chamber being present to attenuate the noise so as to reduce, if not eliminate, bothersome noise to the user causes by the air inflow.

The tortuous air path is located adjacent an air outlet through which air exits the face mask, e.g., under force provided by the fan, and defines at least a portion of an air outflow path along which the air flows from the fan to the air outlet. The tortuous air path has multiple twists and turns, which help attenuate noise of air flowing therethrough.

The noise attenuation system including the acoustic chamber upstream of the fan and the tortuous air path downstream of the fan is one example only. In some implementations, the noise attenuation system includes an acoustic chamber downstream of the fan and a tortuous air path upstream of the fan. In some implementations, the noise attenuation system includes a first acoustic chamber and a first tortuous air path upstream of the fan and a second acoustic chamber and a second tortuous air path downstream of the fan. In some implementations, the noise attenuation system includes a first acoustic chamber upstream of the fan and a second acoustic chamber and a tortuous air path downstream of the fan. In some implementations, the noise attenuation system includes a first tortuous air path upstream of the fan and an acoustic chamber and a second tortuous air path downstream of the fan. In some implementations, the noise attenuation system includes a first acoustic chamber and a tortuous air path upstream of the fan and a second acoustic chamber downstream of the fan. In some implementations, the noise attenuation system includes an acoustic chamber and a first tortuous air path upstream of the fan and a second tortuous air path downstream of the fan.

The noise attenuation system including at least one of an acoustic chamber and a tortuous air path along each of the inflow and outflow air paths is configured to help reduce noise caused by each of air inflow and air outflow. However, in some implementations, the noise attenuation system includes at least one of an acoustic chamber and a tortuous air path along only one of the inflow and outflow air paths, such as due to space constraints of a particular face mask, cost constraints of a particular face mask, or other reason. For example, the noise attenuation system can include an acoustic chamber upstream of the fan. For another example, the noise attenuation system can include an acoustic chamber downstream of the fan. For yet another example, the noise attenuation system can include a tortuous air path upstream of the fan. For still another example, the noise attenuation system can include a tortuous air path downstream of the fan. For another example, the noise attenuation system can include an acoustic chamber and a tortuous air path upstream of the fan. For yet another example, the noise attenuation system can include an acoustic chamber and a tortuous air path downstream of the fan.

In some implementations, the noise attenuation system includes, in addition to at least one of an acoustic chamber and a tortuous air path, a flared acoustic waveguide at the air inlet and/or a flared acoustic waveguide at the air outlet. The flared acoustic waveguide at the air inlet is located at an interface between the air inflow path and an external environment from which air flows into the face mask. The flared acoustic waveguide at the air inlet may thus reduce low-frequency sound radiation into the external environment, and thus to the user's ears, from the air inlet. The flared acoustic waveguide at the air outlet is located at an interface between the air outflow path and the external environment to which air exits from the face mask. The flared acoustic waveguide at the air outlet may thus reduce low-frequency sound radiation into the external environment, and thus to the user's ears, from the air outlet.

In an exemplary implementation, whether or not the noise attenuation system includes at least one flared acoustic waveguide, the face mask's air inlet and air outlet are both located at a bottom of the face mask. Noise from air entering the air inlet and noise from air exiting the air outlet may thus be directed away from the user's ears, which are located by opposed left and right sides of the mask. Higher frequencies are more directional in nature than lower frequencies and thus tend to travel in a straight line. Noise at higher frequencies may thus tend more to be directed away from the user's ears by the at least one flared acoustic waveguide. In some implementations, instead of being located at the bottom of the face mask, one or both of the air inlet and air outlet are located at a top of the face mask, which is configured to direct air away from the user's ears similar to being located at the bottom of the face mask.

FIG. 1 illustrates one exemplary implementation of a face covering device (also referred to herein as a "face mask" or "mask") 100 configured to provide cooling therapy to a user wearing the face covering device 100. The face covering device 100 in this illustrated implementation is also configured to provide light therapy. The methods, systems, and devices described herein also apply to face covering devices that are configured to provide cooling therapy without being configured to provide light therapy.

The mask 100 includes a base 102 and a support 104 attached to the base 102. The base 102 is configured to be worn over a user's face. The support 104 is configured to be worn on the user's head to support the mask 100, and thus the base 102, on the user's head.

The support 104 can have a variety of configurations. For example, the support 104 can include a cap configured to be worn on a user's head similar to a hat. For another example, as in this illustrated implementation, the support 104 can include a strap assembly including a first strap 104*a* and a second strap (obscured in FIGS. 1 and 2) attached to the first strap 104*a*. The first strap 104*a* is an upper portion of the strap assembly and is configured to be worn over and extend front-back along a crown of a user's head. The second strap is a lower portion of the strap assembly and is configured to be worn around and extend substantially horizontally along a partial circumference of the user's head. The second strap's extension may not be precisely horizontal but nevertheless be considered to be substantially horizontal, depending on a particular user's head and how a user positions the second strap. In an exemplary implementation, the first strap 104 and the second strap are made from a flexible material, e.g., a textile, a plastic, or a combination thereof, which may help the first strap 104*a* and the second strap comfortably conform to a size and shape of particular user's head.

In some implementations, the strap assembly includes padding, e.g., foam, air pockets, or other padding, configured to be positioned between the user's head and each of the strap assembly's straps to provide increased user comfort.

The strap assembly includes an adjustment mechanism, such as a buckle, snaps, Velcro, or other adjustment mechanism, configured to allow manual user adjustment of the first strap 104*a* and the second strap to help fit the mask 100 snugly and comfortably on the user. In other implementations, the strap assembly is self-adjusting, such as by straps of the strap assembly being elastic members similar to an elastic headband.

Figure 2:
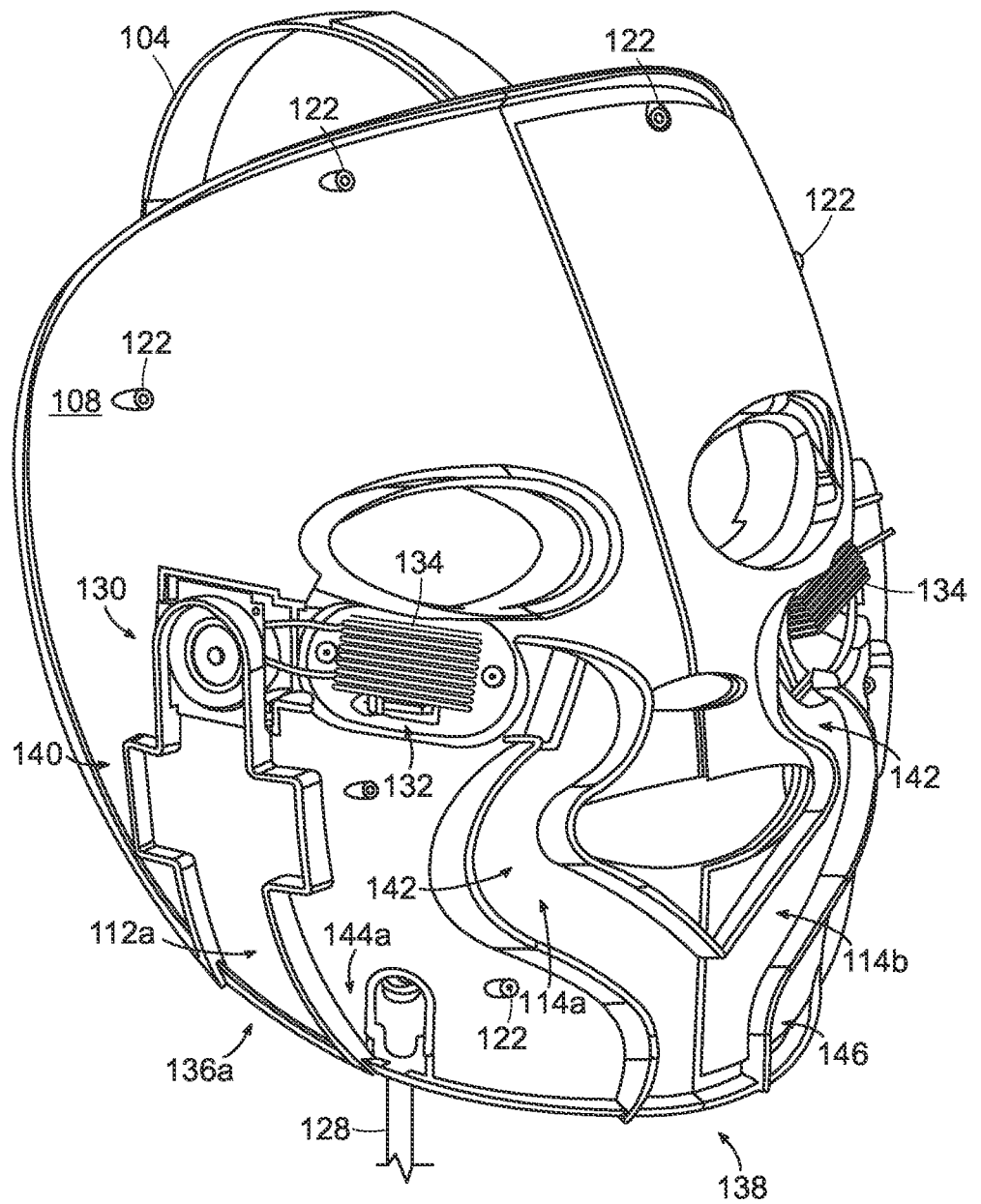
FIG. 2 is a perspective view of a portion of the face mask of FIG. 1.
Figure 3:
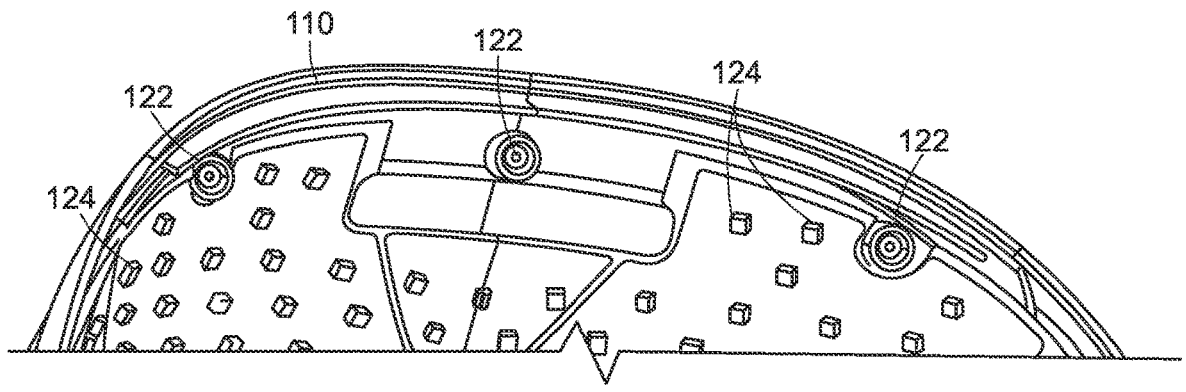
FIG. 3 is a perspective view of an intermediate shell of the face mask of FIG. 1.

As shown in FIGS. 1-3, the base 102 includes an outer shell 106, an inner shell 108, and an intermediate shell 110 located between the outer and inner shells 106, 108. The intermediate shell 110 is only partially shown in FIG. 3, with an upper portion of the intermediate shell 110 being shown. In an exemplary implementation, the base 102 is made from a rigid material, e.g., a plastic, a metal, or a combination thereof, which may help prevent the mask 100 from bending, deflecting, twisting, or otherwise breaking and/or may help prevent the mask's first and second air inflow paths 112*a* and first and second air outflow paths 114*a*, 114*b*, which are defined by ducting formed between the outer and inner shells 106, 108, from deforming, twisting, or otherwise becoming at least partially obstructed so as to impede air flow. The second air inflow path is obscured in the figures.

The base 102 has a plurality of openings 116*a*, 116*b*, 118, 120 formed therein that each corresponds to a face feature and is configured to align at least partially with the face feature when the mask 100 is worn by a user. In this way, with a user wearing the mask 100, each of the plurality of openings 116*a*, 116*b*, 118, 120 will align at least partially with a feature of the user's face. Each of the plurality of openings 116*a*, 116*b*, 118, 120 is formed through all of the outer, inner, and intermediate shells 106, 108, 110. The plurality of openings include a first eye opening 116*a* configured to align at least partially with a right eye of a user wearing the mask 100, a second eye opening 116*b* configured to align at least partially with a left eye of the user wearing the mask 100, a nose opening 118 configured to align at least partially with a nose of the user wearing the mask 100, and a mouth opening 120 configured to align at least partially with a mouth of the user wearing the mask 100. The first and second eye openings 116*a*, 116*b* are configured to allow the user to see while wearing the mask 100 without the mask 100 preventing the user from being able to see anything except an inside surface of the mask 100, e.g., an inside surface of the inner shell 108. The nose opening 118 is configured to allow the user to easily use through their nose, e.g., for breathing, etc., while the user is wearing the mask 100. The mouth opening 120 is configured to allow the user to easily use their mouth, e.g., for breathing, drinking, eating, etc., while the user is wearing the mask 100.

All of the plurality of openings 116*a*, 116*b*, 118, 120 in this illustrated implementation are unobstructed openings. In other implementations, one or more of the plurality of openings 116*a*, 116*b*, 118, 120 can be at least partially obstructed, such as with mesh, a transparent polymer plate, or other obstruction element.

The base 102 in this illustrated implementation is configured to cover substantially all of a user's face with the user wearing the mask 100. The base 102 may not entirely cover a particular user's face depending on a size and shape of the particular user's face, but the base 102 has a size configured to cover faces of most potential users of the mask 100. The base 102 thus includes openings 116*a*, 116*b*, 118, 120 for all of the user's eyes, nose, and mouth. In some implementations, the base 102 is configured to partially cover a user's face, such as only cover an upper half of a user's face, only cover a lower half of a user's face, cover a user's face except for left and right cheeks, or other partial coverage configuration. In such implementations, the base 102 may not have at least one of the eye, nose, and mouth openings 116*a*, 116*b*, 118, 120 depending on where the mask 100 is intended to be placed over a user's face.

The outer shell 106 defines an exterior surface of the mask 100 that faces away from a user's face with the user wearing the mask 100. The inner shell 108 defines an interior surface of the mask 100 that faces toward a user's face with the user wearing the mask 100. The intermediate shell 110 is sandwiched between the outer and inner shells 106, 108. FIGS. 2 and 3 illustrate a plurality of interior connection points 122 at which the outer, inner, and intermediate shells 106, 108, 110 are configured to be securely attached together, such as by using pins, adhesive, welding, etc. The illustrated mask 100 includes eight interior connection points 122, but another number of interior connection points 122 can be used.

A light assembly is located on the intermediate shell 110. The light assembly is configured to apply light therapy to a user wearing the mask 100. The light assembly includes a plurality of lights 124 spaced apart from one another in a pattern, e.g., a grid pattern, a random pattern, or other pattern, on the intermediate shell 110. FIG. 3 shows only some of the mask's lights 124.

The light 124 are configured to be selectively turned on by a user, to provide the light therapy, and off by the user, to not be providing the light therapy. The lights 124 are light emitting diodes (LEDs) in this illustrated implementation. A number of the lights 124 can be, for example, in a range between ten and two hundred; in a range between fifty diodes and one hundred fifty; in a range between sixty and one hundred; in a range between seventy-five and eighty-five; fifty; seventy-five; eighty; eighty-five; or other number.

Each of the lights 124 is configured to emit light at a predetermined wavelength configured to facilitate various light therapies, such as one or more of an anti-aging treatment and an anti-breakout treatment. The predetermined wavelength can be, for example, a wavelength in a range between about 300 nm and about 1000 nm. The light emitted by the plurality of lights 124 is configured to reach one or more layers of skin, e.g., an epidermis, a dermis, and/or a hypodermis, of a user wearing the mask 100. The layer(s) of skin reached by the light corresponds to the wavelength. For example, a longer wavelength of light is configured to reach a deeper layer of skin than a shorter wavelength of light. In some implementations, the wavelength emitted by the lights 124 is configured to be adjustable, such as by one or more of a user manually selecting the wavelength and a wireless computing device configured to wirelessly communicate with a controller of the face covering device 100 to allow a user to manually select the wavelength.

Figure 4:
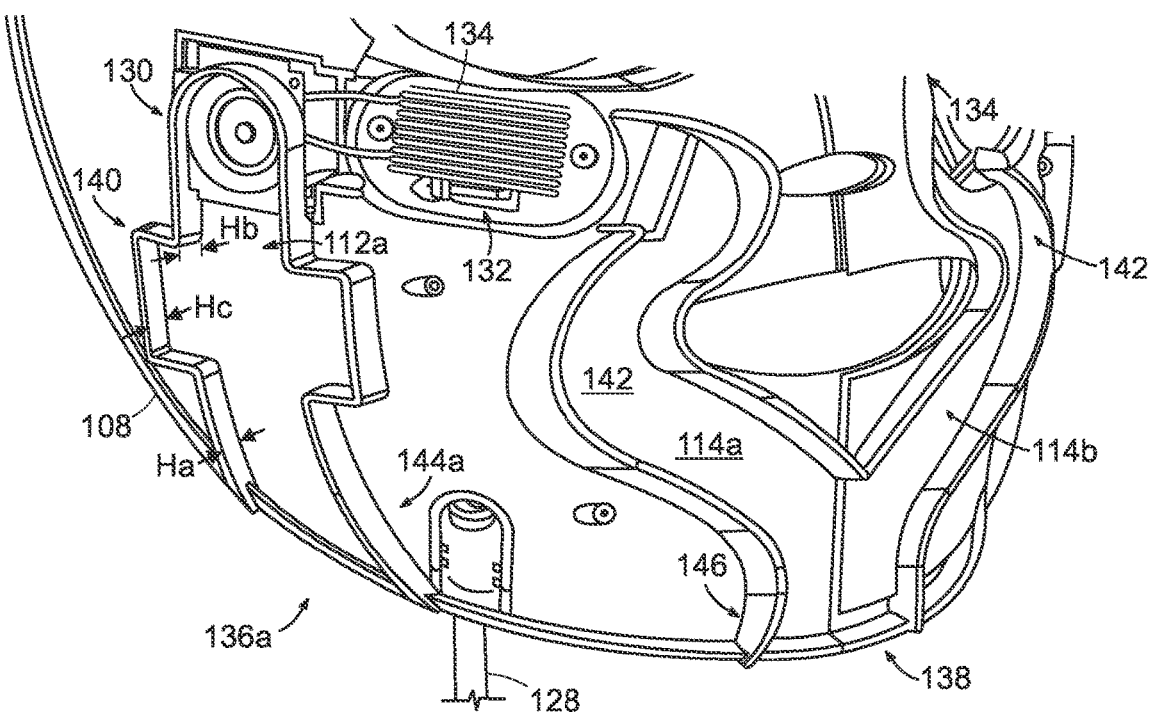
FIG. 4 is a perspective view of another portion of the face mask of FIG. 1.
Figure 5:
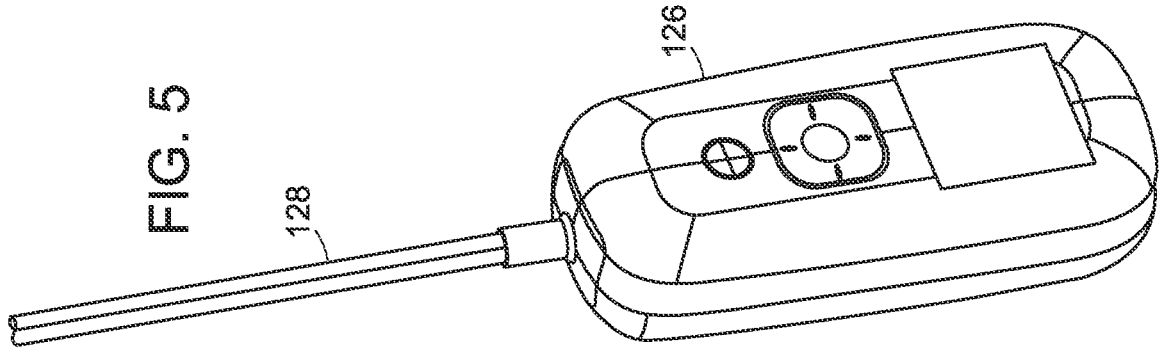
FIG. 5 is a perspective view of one implementation of a control unit operably coupled with the face mask of FIG. 1.

As shown in FIG. 5, a control unit 126 is connected to the mask 100. The control unit 126 is configured to allow a user to control various functions of the mask 100. The control in this illustrated implementation includes control of the light therapy (e.g., turning the lights 124 on/off and adjusting light wavelength) and control of the cooling therapy (e.g., turning cooling therapy on/off and adjusting cooling strength). The control unit 126 is connected to the mask 100 with a cable 128. FIG. 5 shows the cable 128 connected at one end of the cable 128 to the control unit 126. FIGS. 1, 2, and 4 show the other, opposite end of the cable 128 connected to the mask 100.

The control unit 126 in this illustrated implementation is a dedicated control unit for the mask 100 and thus cannot control other masks 100 or other devices. In other implementations, the control unit 126 is a dedicated control unit for the mask 100 but is a wireless remote control connected wirelessly to the mask 100, e.g., via Bluetooth or other wireless communication protocol. In still other implementations, the control unit 126 is not a dedicated control unit for the mask 100 and can control other masks and/or other devices. Examples of non-dedicated control units include a mobile phone, a mobile tablet, and other computing devices configured to wirelessly communicate with the mask 100.

The control unit 126 includes a power source (obscured in FIG. 5), such as a battery or other power source, configured to provide power to the lights 124 of the mask 100 and to a cooling system of the mask 100, which is discussed further below. The control unit 126 including the power source may help reduce a weight and/or bulkiness of the mask 100, which may provide for a better user experience. In other implementations, the mask 100 includes a power source instead of or in addition to the control unit 126.

Figure 6:
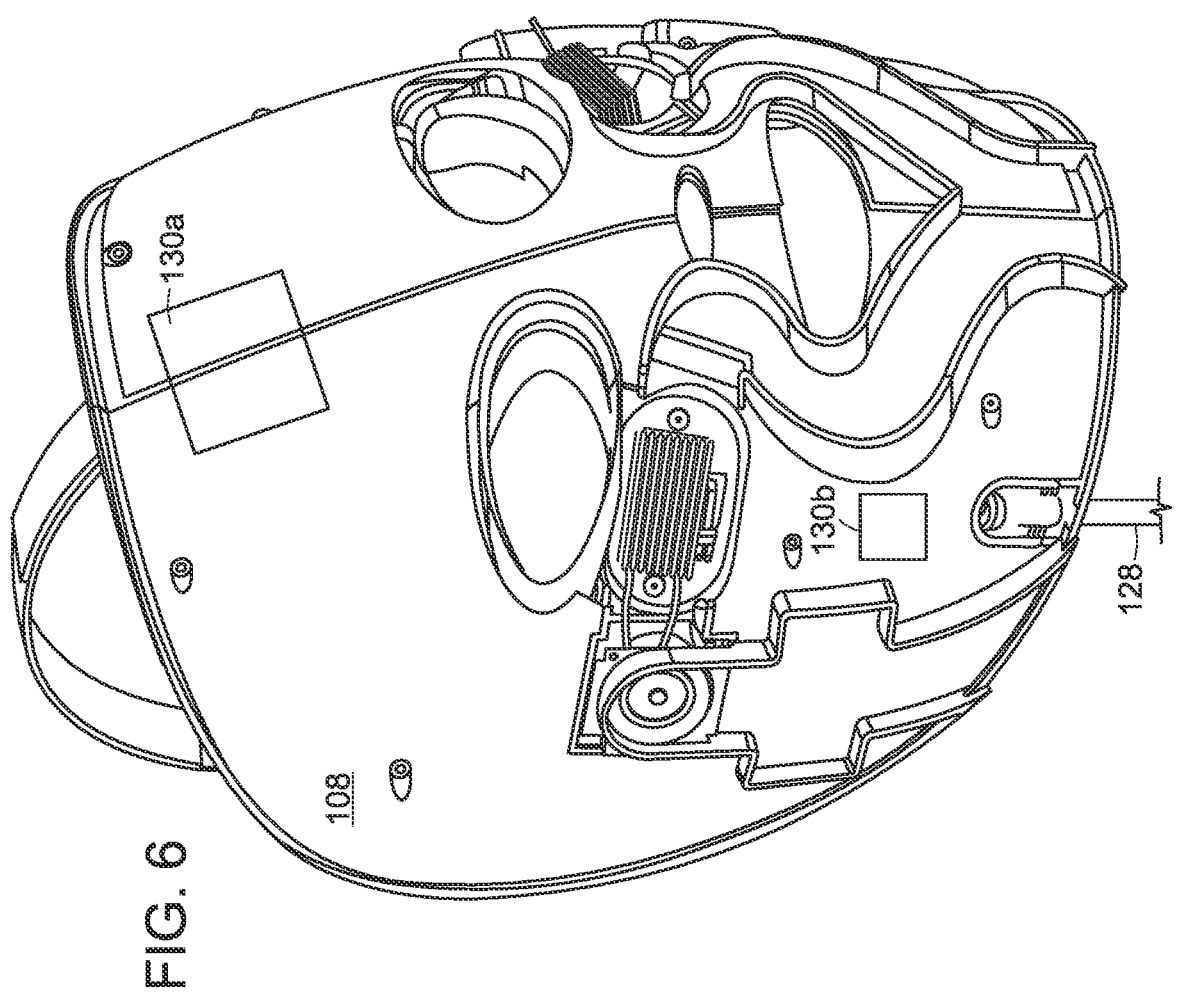
FIG. 6 is a perspective view of the portion of the face mask of FIG. 2 illustrating example locations of a printed circuit board (PCB) of the face mask.

The mask 100 includes a controller (e.g., a processor, a microcontroller, or other electronic controller) configured to be in operable communication with the control unit 126. In an exemplary implementation, the mask 100 includes a printed circuit board (PCB) that includes the controller. FIG. 6 illustrates two example locations of a PCB 130a, 130b. Each of the locations is on an exterior surface of the inner shell 108, e.g., a surface facing away from a user's face with the user wearing the mask 100, but the PCB, and thus the controller, can be secured to the mask 100 elsewhere. FIG. 6 shows the PCB 130a in an upper portion of the mask 100 in a forehead area of the mask 100. Because of the relatively large amount of surface area in the forehead area of the mask 100, the PCB 130a being located in the upper portion may allow for a larger, and thus more powerful, controller and associated PCB components (e.g., memory, bus, transceiver or other wireless communication unit, etc.). FIG. 6 shows another location of the PCB 130b in a lower portion of the mask 100 in a chin area of the mask 100. The cable 128 extends from the lower portion of the mask 100, so the PCB

130b being in the lower portion may ease manufacturing of the mask 100 for operable coupling of the control unit 126 and the controller.

In some implementations, the control unit 126 includes the PCB, and thus the controller, instead of the mask 100.

As mentioned above, the mask 100 includes a cooling system configured to provide cooling therapy to a user wearing the mask 100, such as one or more of an anti-aging treatment and an anti-breakout treatment. As in this illustrated implementation, as shown in FIGS. 2, and 4, the cooling system can include a fan 130, a thermoelectric cooling device 132, such as a Peltier device, a TEC, or other thermoelectric cooling device, and a heat sink 134. The thermoelectric cooling device 132 is a Peltier device in this illustrated implementation.

The mask 100 can include a single cooling system or, as in this illustrated implementation, can include a plurality of cooling systems. The illustrated mask 100 includes two cooling systems, a first cooling system and a second cooling system. The first cooling system is associated with a right side of the mask 100 and thus with a right side of a user's face when the mask 100 is on the user's face. The second cooling system is associated with a left side of the mask 100 and thus with a left side of the user's face when the mask 100 is on the user's face. The mask 100 therefore includes first and second fans 130, first and second thermoelectric cooling devices 132, and first and second heat sinks 134. The second fan and the second thermoelectric cooling device are obscured in the figures. The first and second cooling systems are configured and used similarly so are not each particularly described, with features described for the first cooling system similarly applying to the second cooling system.

The first thermoelectric cooling device 132 is configured to generate heat through a thermoelectric effect where a heat flux is created at a junction of two different types of materials, as will be appreciated by those skilled in the art. The heat flux creates a cold area and a hot area. The cold area is configured to face toward the user's face when the mask 100 is on the user face to provide cool energy to the user's skin. The hot area is configured to face away from the user's face, when the mask 100 is on the user face, to urge heat away from the user's skin. The first heat sink 134 faces the hot area of the first thermoelectric cooling device 132 to help the first heat sink 134 to receive heat energy from the first thermoelectric cooling device 132, e.g., from the hot area thereof, to help prevent the heat from being applied to the user's face or interfering with the cooling effect provided to the user's skin via the first thermoelectric cooling device 132.

The heat sink 134 is located downstream of the first fan 130. The first fan 130 is configured to blow air toward the first heat sink 134. The first fan 130 is thus configured to help dissipate the heat created by the thermoelectric cooling device 132. Heat is therefore urged away from the first heat sink 134 and out of the mask 100. The first fan 130 is operably coupled with the mask's controller to allow the controller to control the first fan 130, e.g., on/off status of the first fan 130, etc.

The mask 100 includes the first air inflow path 112a, along which air enters the mask 100 through a first air inlet 136a and travels to the first fan 130, and the first air outflow flow path 114a, along which air travels from the first fan 130 to the first heat sink 134 and exits the mask 100 through an air outlet 138. The first air inflow path 112a and the first air outflow path 112b thus define an air flow path through the mask 100 from the first air inlet 136a to the air outlet 138.

The air outlet 138 is a shared air outlet as also being the outlet of the mask's second air outflow path 114b. The second air inlet, through which air is configured to enter the second air inflow path, is obscured in the figures. In other implementations, the mask 100 can have separate air outlets for each of the first and second air outflow paths.

The first and second air inlets 136a and the air outlet 138 are located at a bottom of the mask 100, as shown in FIGS. 2 and 4. Thus, as indicated by FIG. 1, the first and second air inlets 136a and the air outlet 138 are not visible when looking at a front of the mask 100, which may improve aesthetics of the mask 100. In other implementations, any one or more of the first and second air inlets 136a and the air outlet 138 can be located at a top of the mask 100 instead of at the bottom of the mask 100 and may thus similarly not be visible when looking at a front of the mask 100.

As discussed herein, the running of the first and second fans 130, e.g., when the fans 130 are on and causing air flow along the first and second air flow paths, creates noise that can irritate the user wearing the mask 100. The mask 100 includes first and second noise attenuation systems associated with the first and second fans 130, respectively. The first and second noise attenuation systems are configured to attenuate the generated noise that is radiated into the environment due to use of the first and second fans 130, respectively. The first and second noise attenuation systems are configured and used similarly so are not each particularly described, with features described for the first noise attenuation system similarly applying to the second noise attenuation system.

In this illustrated implementation, as shown in FIGS. 2 and 4, each of the first and second noise attenuation systems includes an acoustic chamber 140 upstream of its associated fan 130 and a tortuous air path 142 downstream of its associated fan 130. The second acoustic chamber associated with the second air flow path is obscured in the figures.

The first acoustic chamber 140 is generally configured as silencers configured to muffle sound. As shown in FIGS. 2 and 4, the first acoustic chamber 140 is located adjacent the air inlet 136a. Air is thus configured to enter the first air inlet 136a and flow into the first acoustic chamber 140.

The inner shell 108 forms an inner side of the first acoustic chamber 140, as shown in FIGS. 2 and 4. The intermediate shell 110 and/or the outer shell 108 form an outer side of the first acoustic chamber 140. An inlet end of the first acoustic chamber 140 that is in fluid communication with the first air inlet 136a is open to allow acoustic energy to enter the first acoustic chamber 140. An outlet end of the first acoustic chamber 140 is open to allow acoustic energy to exit the first acoustic chamber 140 in a direction toward the first fan 130.

Figure 7:
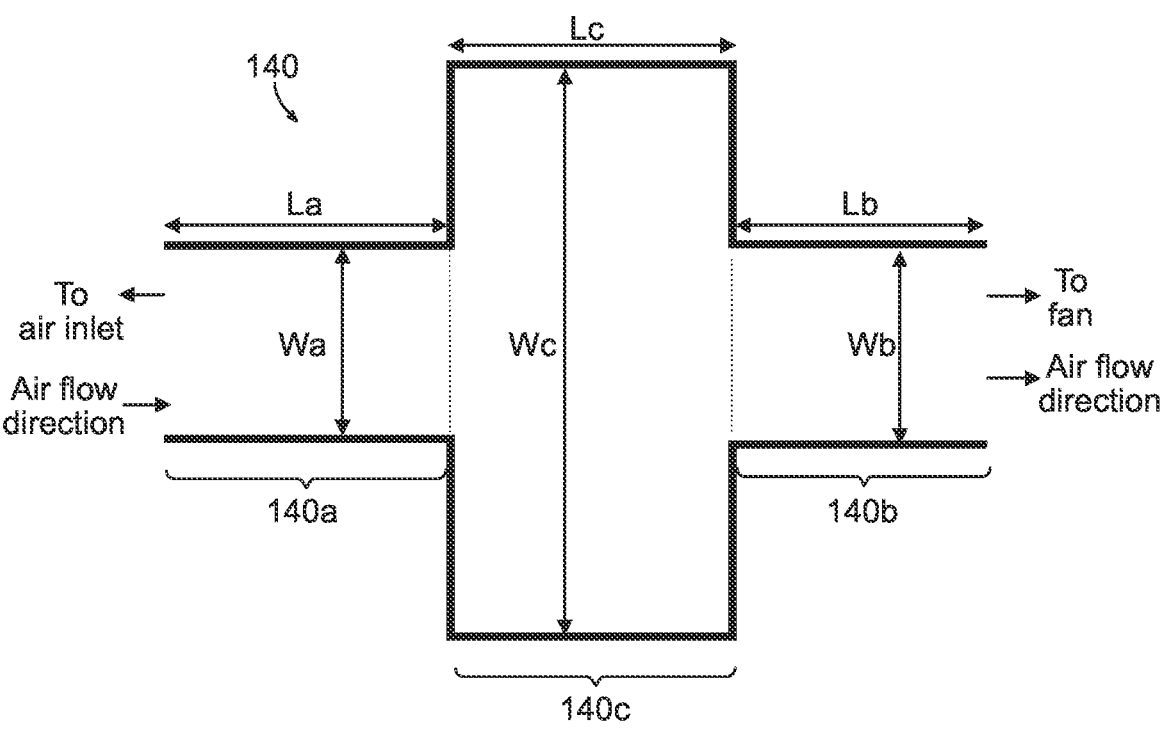
FIG. 7 is a schematic view of an acoustic chamber of the face mask of FIG. 1.

As shown in FIG. 7, the first acoustic chamber 140 includes an inlet chamber 140a, an outlet chamber 140b, and a central chamber 140c that is located between and is in fluid communication with the inlet and outlet chambers 140a, 140b. The central chamber 140c is also referred to herein as an "expansion chamber," as the central chamber 140c has a width Wc that is greater than, or expanded, as compared to widths Wa, Wb of the inlet and outlet chambers 140a, 140b.

Air flow direction through the first acoustic chamber 140 is shown with arrows in FIG. 7. Air entering the mask 100 through the first air inlet 136a is configured to enter the first acoustic chamber 140 at the inlet chamber 140a, flow through the inlet chamber 140a to the central chamber 140c, flow through the central chamber 140c to the outlet chamber 140b, and through the outlet chamber 140b to the first fan 130.

A difference in cross-sectional area of each adjacent chamber 140a, 140b, 140c of the first acoustic chamber 140 creates a difference in acoustic impedance at each chamber interface, e.g., an interface between the inlet and central chambers 140a, 140c and an interface between the central and outlet chambers 140c, 140b. The difference in acoustic impedance causes some frequencies to be transmitted and others to be reflected back to the source, e.g., in a direction toward the first air inlet 136a. The first acoustic chamber 140 can thus act as a low-pass filter, allowing only low frequencies to pass through. With the first fan 130 on such that air is drawn into the mask 100 through the first air inlet 136a, the first acoustic chamber 140 may thus significantly reduce sound pressure transmitted from the mask 100 to a user wearing the mask 100.

The first acoustic chamber 140 has dimensions tuned to maximize noise reduction in a desired frequency band, e.g., a frequency band sensitive to human hearing. Humans are more sensitive to sound frequencies between 2000 and 5000 Hz. Thus, in an exemplary implementations, the dimensions of the first acoustic chamber 140 are selected to reduce noise of sound frequencies between 2000 and 5000 Hz.

Each of the inlet, outlet, and central chambers 140a, 140b, 140c has a substantially rectangular cross-sectional shape in this illustrated implementation, as shown in FIG. 7. A person skilled in the art will appreciate that a shape may not be precisely that shape but nevertheless be considered to be substantially that shape for any number of reasons, such as manufacturing tolerances and sensitivity of measurement equipment. As mentioned above, and as shown in FIG. 7, the inlet, outlet, and central chambers 140a, 140b, 140c each has a width Wa, Wb, Wc. As shown in FIGS. 4 and 7, the inlet, outlet, and central chambers 140a, 140b, 140c each has a length La, Lb, Lc and a height Ha, Hb, Hc.

Figure 8:
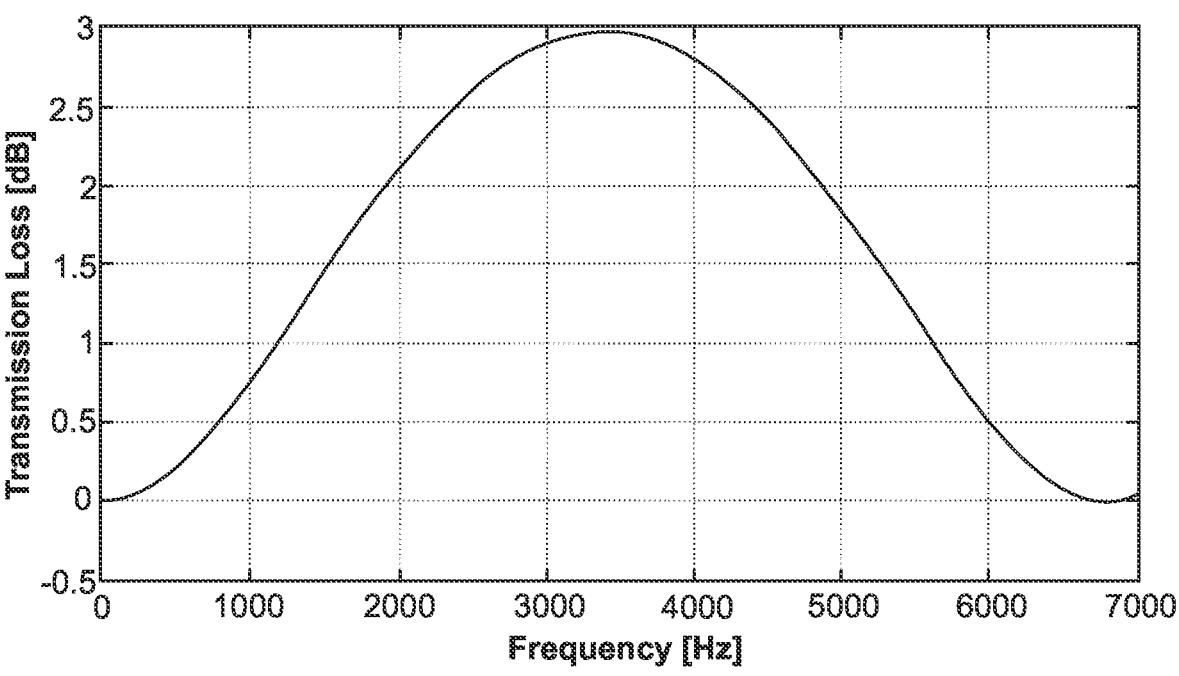
FIG. 8 is a graph showing transmission loss versus frequency.

In an exemplary implementation, the inlet and outlet chamber widths Wa, Wb are each about 25.4 mm, the central chamber width Wc is about 60.5 mm, the inlet, outlet, and central chamber heights Ha, Hb, Hc are each about 3 mm, and the length Lc of the central chamber 140c is about 25.3 mm. Such dimensions tune the acoustic chamber 140 to 3500 Hz, as shown in FIG. 8 where a peak of about 3 dB of noise reduction is achieved at about 3500 Hz. About 3500 Hz is midway between 2000 Hz and 5000 Hz and is the frequency at which the length Lc of the central chamber 140c matches ¼ of its wavelength. Changing the length Lc of the central chamber 140c changes where the curve of the graph peaks or, in other words, where the acoustic chamber 140 is tuned. The magnitude of noise reduction is also adjustable by changing a ratio of the central chamber width Wc to the inlet and outlet chamber widths Wa, Wb. The higher this ratio, the more noise reduction is achieved. In the above example, the ratio of the central chamber width Wc to the inlet and outlet chamber widths Wa, Wb is 2.4, which is 60.5/25.4. Thus, in an exemplary implementation, to tune the first acoustic chamber 140 to reduce noise most in the most sensitive human range between 2000 and 5000 Hz, the ratio of the central chamber width Wc to the inlet and outlet chamber widths Wa, Wb is selected to be at least about 2, e.g., about 2.4.

In other implementations, the first acoustic chamber 140 can include two or more central chambers, each connected to inlet/outlet chambers with significantly larger or smaller cross-sectional areas to provide a difference in acoustic impedance. For example, the first acoustic chamber 140 can include an inlet chamber fluidly connected to a first central chamber, which is fluidly connected to a first outlet chamber, which is fluidly connected to a second central chamber, which fluidly is connected to a second outlet chamber, though which air flows toward the first fan 130.

In some implementations, the first acoustic chamber 140 can include internal baffles or other internal structures configured to direct acoustic energy through the first acoustic chamber 140 as desired.

Acoustic chambers and acoustic energy are further discussed, for example, in U.S. patent application Ser. No. 18/103,720 entitled "Acoustic Muffler For A Motorized Food Processing Device" filed Jan. 31, 2023, which is hereby incorporated by reference in its entirety.

The first and second tortuous air paths 142 are generally configured to provide physical barriers for acoustic energy and thus prevent sound from escaping, e.g., from exiting the mask 100 out of the air outlet 138. As shown in FIGS. 2 and 4, the first and second tortuous air paths 142 are each located adjacent the air outlet 138. Air is thus configured to enter the first and second tortuous air paths and flow out of the air outlet 138. The first and second tortuous air paths 142 are mirror images of one another and join together near the air outlet 138.

The first and second tortuous air paths 142 each has multiple twists and turns, each of which helps attenuate noise of air flowing therethrough. Each twist and turn provides a physical barrier against which sound energy will hit, with some of the sound energy bouncing backward, e.g., away from the air outlet 138. Sound bounced backward can interfere with itself to further reduce noise. Additionally, twists and turns lengthen a path between two points, e.g., between the first fan 130 and the air outlet 138 and between the second fan and the air outlet 138, such that sound has to travel a longer distance to exit the mask 100. Longer path distances inherently reduce noise more than shorter distances. In this illustrated implementation, each of the first and second tortuous air paths 142 is substantially S-shaped with two twists and turns that are each less than 90 degrees, e.g., an angle that is greater than about 20 degrees and is less than about 90 degrees. An angle of greater than 90 degrees would not provide an effective physical barrier and thus not provide effective noise reduction. In other implementations, each of the first and second tortuous air paths can have another number of twists and turns.

In this illustrated implementation, the first and second noise attenuation systems also each include a flared acoustic waveguide. The first noise attenuation system includes a first flared acoustic waveguide 144a at the first air inlet 136 and a second flared acoustic waveguide 146 at the air outlet 138. The first flared acoustic waveguide 144a is located at an interface between the first air inflow path and the external environment from which air flows into the first air inlet 136a. The second flared acoustic waveguide 146 is located at an interface between the first and second air outflow paths and the external environment to which air flows out of the air outlet 138. Each of the first and second flared acoustic waveguides 144a, 146 is configured as an outwardly flared portion of the ducting forming the first air inflow path and the air outflow path, respectively. Thus, the first flared acoustic waveguide 144a has a width that flares outwardly from the width Wa of the inlet chamber 140a so as to increase above the inlet chamber's width Wa.

The second noise attenuation system includes a third flared acoustic waveguide (obscured in the figures) at the second air inlet and the second flared acoustic waveguide 146 at the air outlet 138. The third flared acoustic waveguide is located at an interface between the second air inflow path and the external environment from which air flows into the second air inlet. The third flared acoustic waveguide is configured as an outwardly flared portion of the second air inflow path. The third flared acoustic waveguide has a width that flares outwardly from the width of the second inlet chamber so as to increase above the second outlet chamber's width (which in this illustrated implementation is the same as the first outlet chamber's width Wa since the first and second air inflow paths mirror each other).

The first, second, and third flared acoustic waveguides 144a, 146 act as acoustic horns (also referred to herein as "horns") at their respective interfaces. Acoustic horns increase sound radiation into the environment, such as the flaring out at the ends of trumpets and megaphones. The first and second noise attenuation systems that include the first, second, and third flared acoustic waveguides 144a, 146, however, are configured to reduce noise, not increase noise as with trumpets and megaphones, for example. Geometries of the first, second, and third flared acoustic waveguides 144a, 146 are configured to not allow sound propagation below certain frequencies because, as the frequency of a sound is decreased, the sound wave's phase speed will become an imaginary number. When the phase speed becomes imaginary, the sound wave becomes evanescent such that the sound wave no longer can propagate and instead decays exponentially. The frequency where this transition from travelling wave to evanescent wave is called the horn cutoff frequency. Thus, the first, second, and third flared acoustic waveguides 144a, 146 are configured such that the cutoff frequency, e.g., where an acoustic horn transmission factor is zero, is above a target frequency undesirable to radiate, such that the sound wave will not be able to propagate down the acoustic horn in the first place. The acoustic horn transmission factor is a number from zero to one which describes the ratio of sound that can propagate down an acoustic horn when compared to a straight duct having a same cross-sectional area as the acoustic horn's opening.

Figure 9:
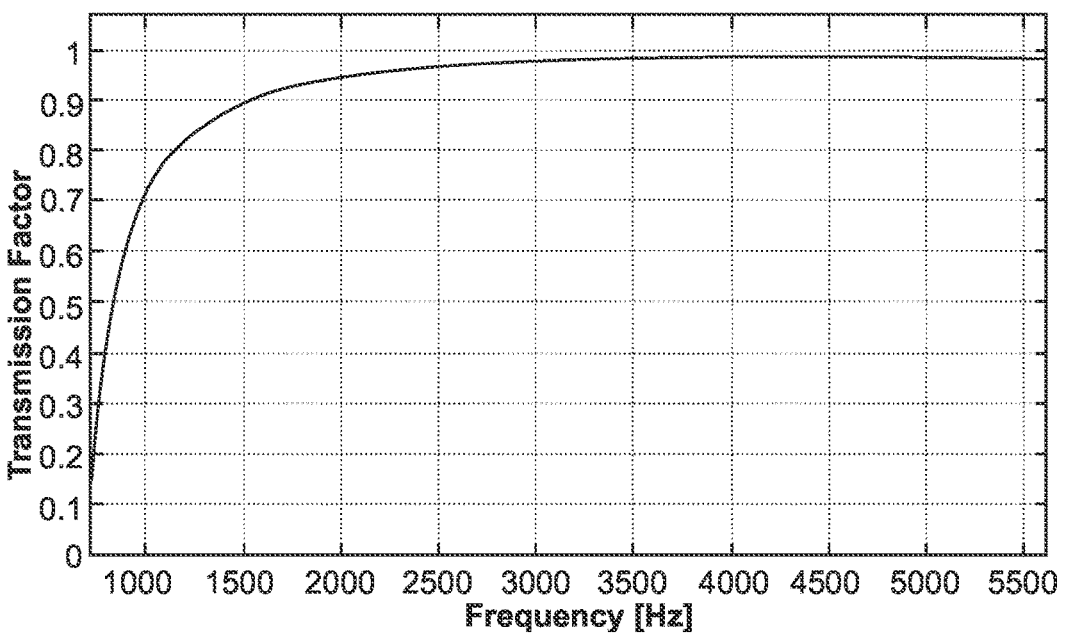
FIG. 9 is a graph showing transmission factor versus frequency.

The running of the first and second fans 130 provides low-frequency noise that is undesirable for a user of the mask 100 to hear. FIG. 9 illustrates one implementation of an acoustic horn transmission factor for the first and third flared acoustic waveguides 144a located at the first and second inlets 136a, respectively. For frequencies below about 5000 Hz, the acoustic horn transmission factor is less than one. Thus, were the first and third flared acoustic waveguides 144a not present and instead a straight tube with a same cross-sectional area was present, more sound below 5000 Hz would be exiting the mask 100 through the first and second air inlets 136a and thus create more noise heard by the user wearing the mask 100. Below about 1000 Hz, there is a steep decline of the sound that can enter the first and second air inlets 136a at all. The acoustic horn transmission factor is zero at about 700 Hz, e.g., the horn can no longer support propagating waves below about 700 Hz at all.

Calculations of the transmission factor shown in FIG. 9 were solved using the following differential equation (the Webster horn equation) that governs plane waves in horns using the Wentzel-Kramers-Brillouin method. In the below equation, y describes the radius of the horn as a function of the distance along its axis x. Further, $k_0$ describes the wave number for a constant-cross section tube defined as the ratio of the angular frequency to the speed of sound. Thus, the transmission factor is a frequency-dependent quantity. This method necessitates circular horns. The first and third flared acoustic waveguides 144a are not circular, but the below equation provides an acceptable approximation.

$$TF = \left. \frac{\sqrt{1 - y''/(yk_0^2)}}{1 - k_0^{-2}\left(\frac{y'}{y}\right)'} \right|_{x=0} \qquad \text{EQUATION 1}$$

The transmission factor dropping to zero is not true of all horns. For example, conical horns (where the cross-sectional area varies linearly along its distance) do not have a cutoff frequency. However, horns where the cross-sectional area varies either quadratically or exponentially with distance will have a cutoff frequency. For the first and third flared acoustic waveguides 144a, the horn's width (w) can be approximated using the following quadratic equation. In this equation, both x and w are in mm.

$$w_{inlet} = 0.0057x^2 + 0.1734x + 26.164 \qquad \text{EQUATION 2}$$

Each acoustic horn of a mask, such as the mask 100, can have an exponential function (Equation 1) or a quadratic area function (Equation 2), as each acoustic horn will have a cutoff frequency such that they inhibit low-frequency sound radiation.

Figure 10:
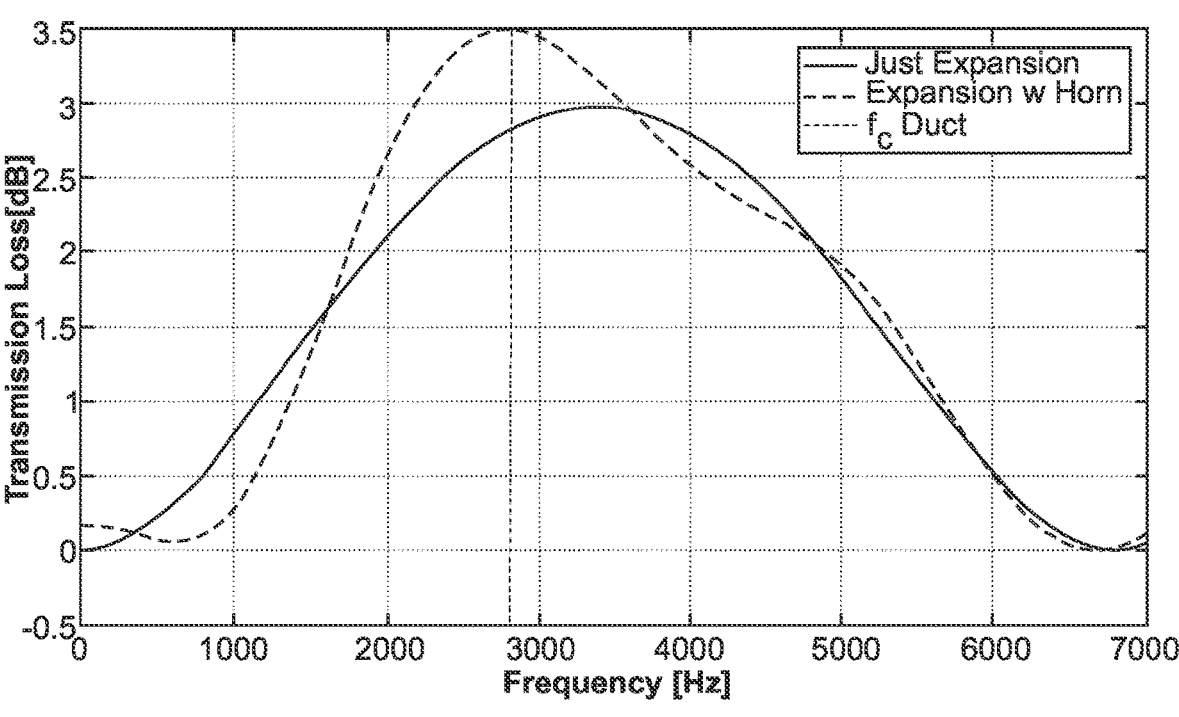
FIG. 10 is another graph showing transmission loss versus frequency.

FIG. 10 illustrates a comparison of sound transmission loss for an implementation of the first air inlet 136a with the first flared acoustic waveguide 144a ("Expansion w/Horn" line in the graph, e.g., the mask 100 includes the first acoustic chamber 140 and the first flared acoustic waveguide 144a) and without the first flared acoustic waveguide 144a ("Just Expansion" line in the graph, e.g., the mask 100 includes the first acoustic chamber 140 but not the first flared acoustic waveguide 144a). FIG. 10 illustrates that that there is a difference between the mask 100 including the first flared acoustic waveguide 144a and not including the first flared acoustic waveguide 144a. FIG. 10 shows differences until about 5000 Hz, when the two versions substantially line back up. As shown in FIG. 9, at about 5000 Hz is when the transmission factor becomes unity again, so the behavior above this point is expected to be the same (not including radiation effects). FIG. 10 also illustrates a boost to noise reduction at lower frequencies in a range of about 1500 and about 3500 Hz with the first flared acoustic waveguide 144a.

Figure 11:
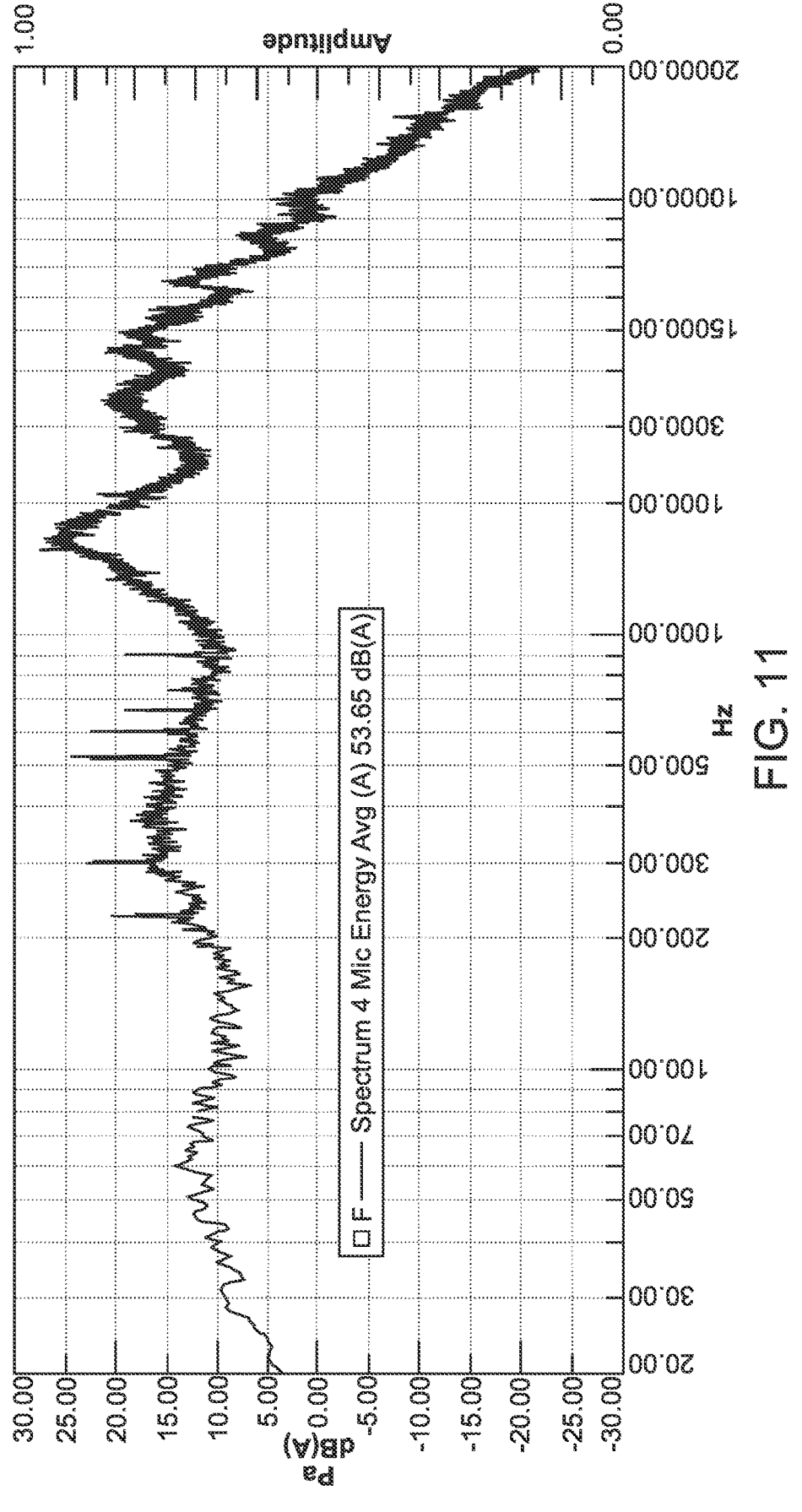
FIG. 11 is a graph showing A-weighted sound pressure level versus frequency.

FIG. 11 illustrates a typical frequency spectrum of the first fan 130. As shown in FIG. 11, most of the noise generated is low frequency noise below about 3000 Hz. In an exemplary implementation, to reduce noise, the first noise attenuation system in relation to the air inlet 136 and the first air inflow path is tuned to reduce noise more effectively in this frequency band below about 3000 Hz, e.g., duct cut off frequency below about 3000 Hz, horn cutoff frequency below about 1000 Hz, length Lc of the expansion chamber 140c being about 25.3 mm, to center the noise reduction band over about 3500 Hz. FIG. 11 also illustrates that there is a steep high-frequency roll-off. Thus, even though an acoustic horn increases radiation efficiency at higher frequencies, the first fan 130 does not produce much high frequency noise.

Figure 12:
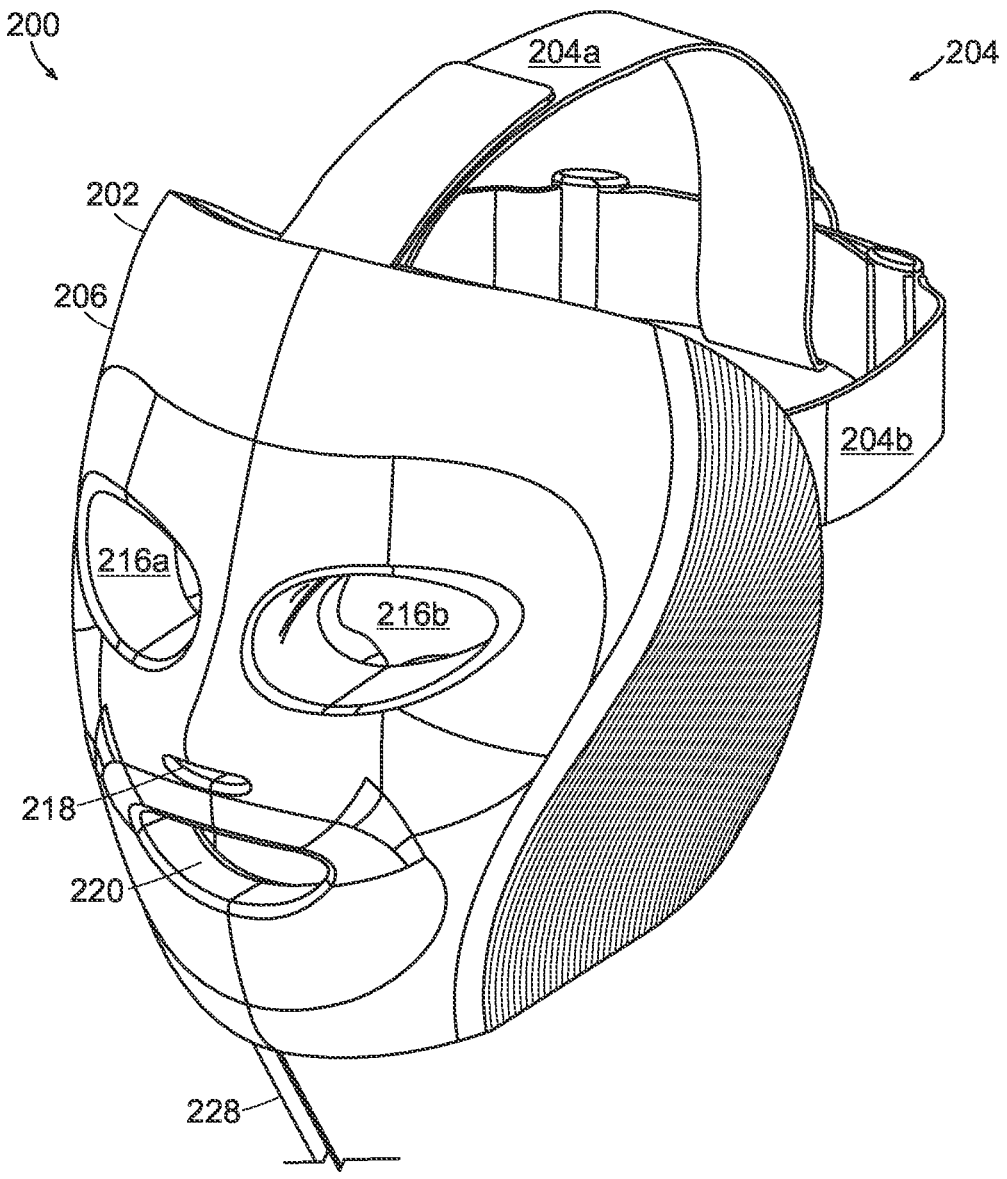
FIG. 12 is a perspective view of another implementation of a face mask.

FIG. 12 illustrates another implementation of a face mask 200 configured to provide cooling therapy to a user wearing the face mask 200. The face mask 200 in this illustrated implementation is also configured to provide light therapy.

Figure 13A:
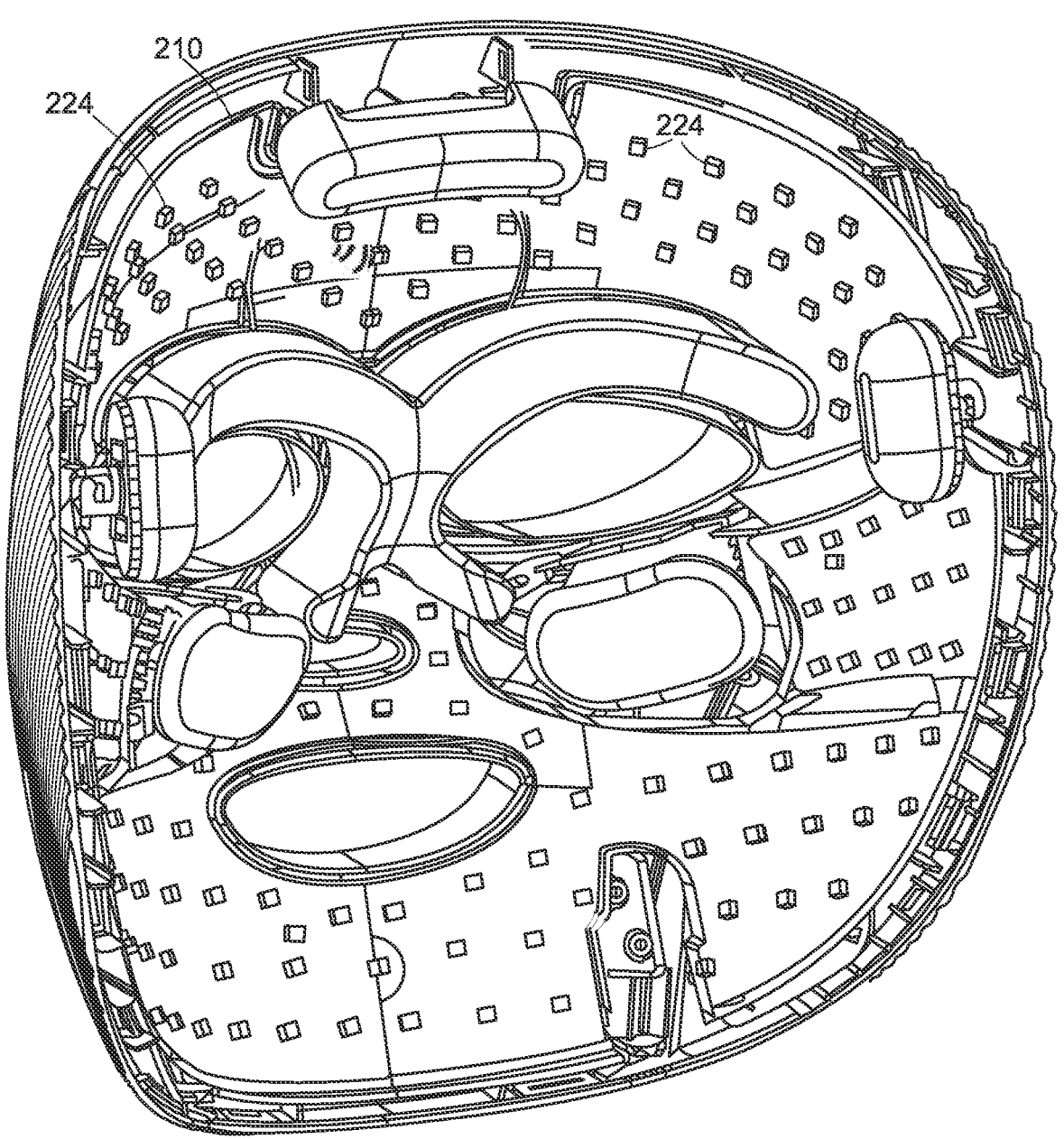
FIG. 13A is a perspective view of an intermediate shell of the face mask of FIG. 12.
Figure 13B:
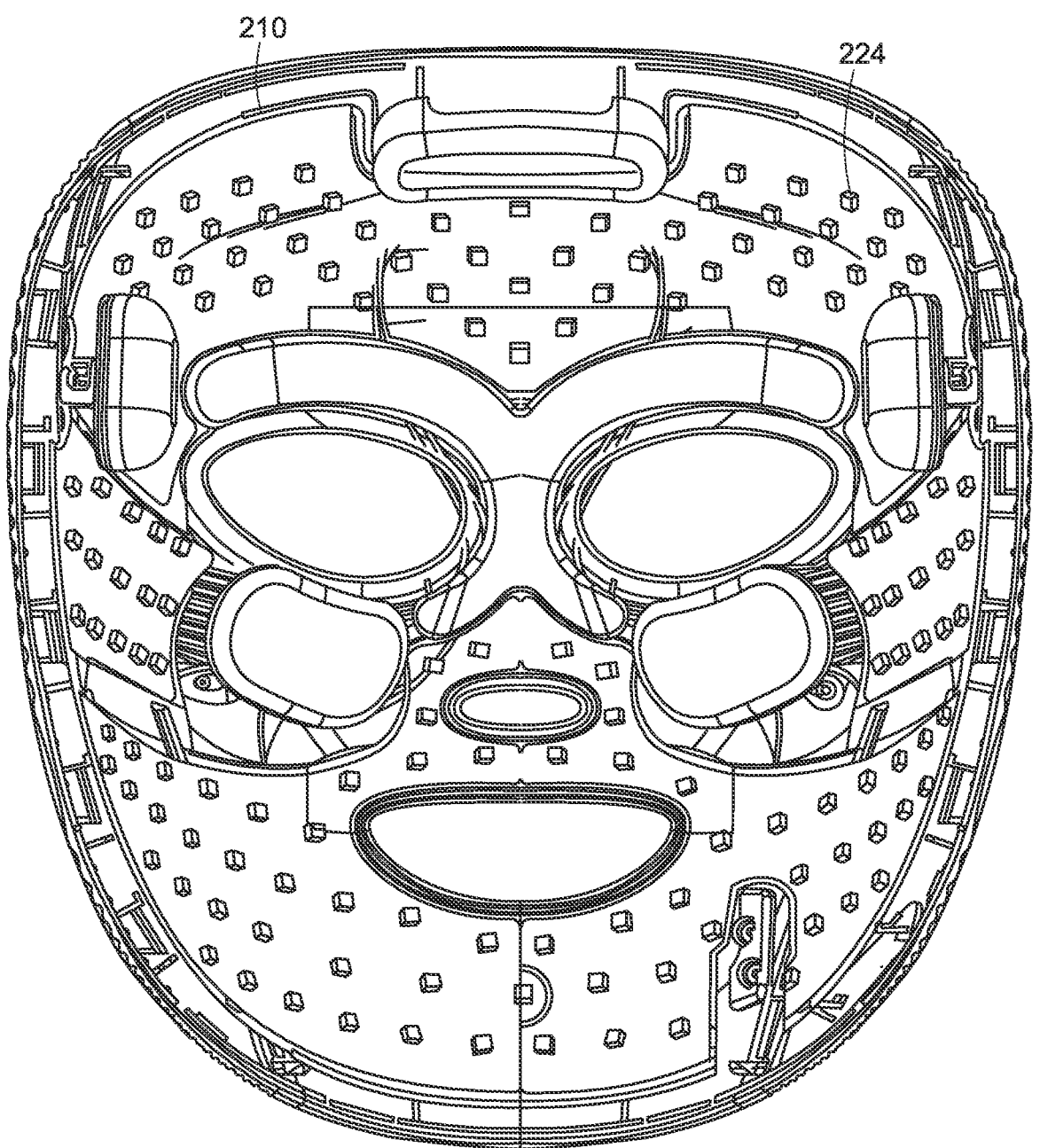
FIG. 13B is another perspective view of the intermediate shell of FIG. 13B.
Figures 14, 15:
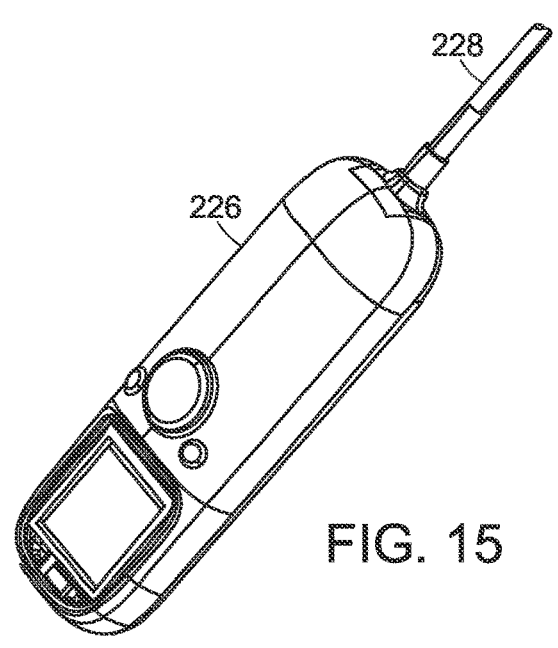
FIG. 14 is a perspective view of a portion of the face mask of FIG. 12.
FIG. 15 is a perspective view of one implementation of a control unit operably coupled with the face mask of FIG. 12.

The face mask 200 of FIG. 12 is generally configured and used similar to the face mask 100 of FIG. 1 and includes a base 202 including an outer shell 206, an inner shell 208 (shown in FIG. 14), and an intermediate shell 210 (shown in FIGS. 13A and 13B); a support 204 including first and second straps 204a, 204b; first and second air inflow paths (obscured in FIG. 12), first and second air outflow paths (obscured in FIG. 12); a plurality of openings including a first eye opening 216a, a second eye opening 216b, a nose opening 218, and a mouth opening 220; a plurality of interior connection points (obscured in FIG. 12); a light assembly includes a plurality of lights 224 (shown in FIGS. 13A and 13B); a PCB (obscured in FIG. 12); first and second cooling systems (obscured in FIG. 12) each including a fan (obscured in FIG. 12, although a fan support 231 configured to seat the fan is shown in FIG. 14), a thermoelectric cooling device, and a heat sink; first and second air inlets (obscured in FIG. 12); a shared air outlet (obscured in FIG. 12); and first and second noise attenuation systems (obscured in FIG. 12) each including an acoustic chamber, a tortuous path, and a flared acoustic waveguide. A control unit 226 (shown in FIG. 15) is operably coupled with the mask 200 using a cable 228 and is generally configured and used similar to the control unit 126 of FIG. 5.

Each of the first and second acoustic chambers of the mask 200 of FIG. 12 is generally configured and used similar to the first and second acoustic chambers 140 of the mask 100 of FIG. 1 but each has a different shape the first and second acoustic chambers 140, as shown in FIG. 14. As shown in FIG. 14, the first acoustic chamber 240 includes an inlet chamber 240a, an outlet chamber 240b, and a central chamber 240c that is located between and is in fluid communication with the inlet and outlet chambers 240a, 240b. The second acoustic chamber mirrors the first acoustic chamber 240. In this illustrated implementation, the central chamber 240c expands laterally to only one side in relation to the inlet and outlet chambers 240a, 240b. The central chamber 140c of the mask 100 of FIG. 1 is expanded laterally to both left and right sides in relation to the inlet and outlet chambers 240a, 240b. The central chamber 240c of FIG. 14 is expanded laterally to the left side, e.g., toward a left side of the mask 200 (e.g., a side of the mask 200 configured to be worn over a left side of a user's face), but the lateral expansion could instead be to a right side. As discussed above, in an exemplary implementation, to tune the first acoustic chamber 240 to reduce noise most in the most sensitive human range between 2000 and 5000 Hz, the ratio of a width of the central chamber 240c to widths of the inlet and outlet chambers 240a, 240b is selected to be at least about 2, e.g., about 2.4.

The subject matter described herein can be implemented in analog electronic circuitry, digital electronic circuitry, and/or in computer software, firmware, or hardware, including the structural means disclosed in this specification and structural equivalents thereof or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, algorithm, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code).

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices). The processor and the memory can be supplemented by, or incorporated in, special purpose logic circuitry.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor-readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor). The modules described herein can be combined, integrated, separated, and/or duplicated to support various applications. Also, a function described herein as being performed at a particular module can be performed at one or more other modules and/or by one or more other devices instead of or in addition to the function performed at the particular module.

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety for all purposes.

The present disclosure has been described above by way of example only within the context of the overall disclosure provided herein. It will be appreciated that modifications within the spirit and scope of the claims may be made without departing from the overall scope of the present disclosure.

What is claimed is:

1. An apparatus with noise attenuation, comprising:
a face mask configured to be worn on a face of a user, the face mask comprising:
  a first air inlet through which air external to the face mask is configured to enter a first flow path,
  an air outlet through which the air is configured to exit the first flow path to exit the face mask,
  a first thermoelectric cooling device configured to generate cooling and to generate heat,
  a first fan configured to cause air to enter the face mask through the first air inlet and to flow along the first flow path from the first air inlet to the first fan and from the first fan along the first flow path to the air outlet, and
  at least one of:
    a first flared acoustic waveguide at the first air inlet,
    a first acoustic chamber along the first flow path and located between the first air inlet and the first fan, and
    a first tortuous path along the first flow path and located between the first fan and the air outlet;
  wherein the cooling is configured to be applied to the face of the user with user wearing the face mask; and
  the air flowing along the first flow path is configured to dissipate the heat.

2. The apparatus of claim 1, wherein the face mask includes at least the first acoustic chamber;
the first acoustic chamber includes a first chamber, a second chamber, and a third chamber;
air is configured to flow from the first air inlet to the first chamber, from the first chamber to the second chamber, and from the second chamber to the third chamber; and
the second chamber is expanded as compared to the first and third chambers.

3. The apparatus of claim 1, wherein the face mask includes at least the first tortuous path; and
the first tortuous path defines a plurality of twists and turns along the first flow path.

4. The apparatus of claim 1, wherein the face mask includes at least the first flared acoustic waveguide; and
the first flared acoustic waveguide is located at an interface between the first air flow path and the first air inlet.

5. The apparatus of claim 1, wherein the first air inlet and the air outlet are located at a bottom of the face mask.

6. The apparatus of claim 1, wherein the face mask further comprises a first heat sink facing the first thermoelectric cooling device and located downstream of the first fan such that the first fan is configured to blow air toward the first heat sink.

7. The apparatus of claim 1, wherein the face mask further comprises a second flared acoustic waveguide at the air outlet.

8. The apparatus of claim 1, wherein the face mask includes at least two of the first flared acoustic waveguide, the first acoustic chamber, and the first tortuous path.

9. The apparatus of claim 1, wherein the face mask includes all of the first flared acoustic waveguide, the first acoustic chamber, and the first tortuous path.

10. The apparatus of claim 1, wherein the face mask further comprises:
a second air inlet through which air external to the face mask is configured to enter a second flow path;
a second thermoelectric cooling device configured to generate cooling and to generate heat;
a second fan configured to cause air to enter the face mask through the second air inlet and to flow along the second flow path from the second air inlet to the second fan and from the second fan along the second flow path to the air outlet; and at least one of:

a second flared acoustic waveguide at the second air inlet, a second acoustic chamber along the second flow path and located between the second air inlet and the second fan, and a second tortuous path along the second flow path and located between the second fan and the air outlet;

the cooling generated by the second thermoelectric cooling device is configured to be applied to the face of the user with user wearing the face mask; and the air flowing along the second flow path is configured to dissipate the heat generated by the second thermoelectric cooling device.

11. The apparatus of claim 10, wherein the face mask includes at least the first acoustic chamber and the second acoustic chamber;

the first acoustic chamber mirrors the second acoustic chamber;

the first acoustic chamber includes a first chamber, a second chamber, and a third chamber;

the second acoustic chamber includes a fourth chamber, a fifth chamber, and a sixth chamber;

air is configured to flow from the first air inlet to the first chamber, from the first chamber to the second chamber, and from the second chamber to the third chamber;

the second chamber is expanded as compared to the first and third chambers;

air is configured to flow from the second air inlet to the fourth chamber, from the fourth chamber to the fifth chamber, and from the fifth chamber to the sixth chamber; and the fifth chamber is expanded as compared to the fourth and sixth chambers.

12. The apparatus of claim 10, wherein the face mask includes at least the first tortuous path and the second tortuous path;

the first tortuous path mirrors the second tortuous path;

the first tortuous path defines a first plurality of twists and turns along the first flow path; and the second tortuous path defines a second plurality of twists and turns along the second flow path.

13. The apparatus of claim 10, wherein the face mask includes at least the first flared acoustic waveguide and the second flared acoustic waveguide;

the first flared acoustic waveguide is located at an interface between the first air flow path and the first air inlet; and the second flared acoustic waveguide is located at an interface between the second air flow path and the second air inlet.

14. The apparatus of claim 10, wherein the first air inlet, the second air inlet, and the air outlet are located at a bottom of the face mask.

15. The apparatus of claim 10, wherein the air outlet is one of:

a shared outlet through which air is configured to exit each of the first and second air flow paths, and first and second air outlets, air being configured to flow through the first air outlet from the first air flow path and through the second air outlet from the second air flow path.

16. The apparatus of claim 10, wherein the face mask further comprises:

a first heat sink facing the first thermoelectric cooling device and located downstream of the first fan such that the first fan is configured to blow air toward the first heat sink; and a second heat sink facing the second thermoelectric cooling device and located downstream of the second fan such that the second fan is configured to blow air toward the second heat sink.

17. The apparatus of claim 10, wherein the face mask includes at least two of the first flared acoustic waveguide, the first acoustic chamber, and the first tortuous path; and the face mask includes at least two of the second flared acoustic waveguide, the second acoustic chamber, and the second tortuous path.

18. The apparatus of claim 10, wherein the face mask includes all of the first flared acoustic waveguide, the first acoustic chamber, and the first tortuous path; and the face mask includes all of the second acoustic waveguide, the second flared acoustic chamber, and the second tortuous path.

19. An apparatus with noise attenuation, comprising:

a face mask configured to be worn on a face of a user, the face mask comprising:

a first thermoelectric cooling device configured to generate cooling and to generate heat, the cooling generated by the first thermoelectric cooling device being configured to be applied to the face of the user with the user wearing the face mask, a first fan configured to cause a first air flow configured to dissipate the heat generated by the first thermoelectric cooling device, a first noise attenuation system configured to attenuate noise caused by the first fan, the first noise attenuation system including at least one of a first flared acoustic waveguide, a first acoustic chamber, and a first tortuous path;

a second thermoelectric cooling device configured to generate cooling and to generate heat, the cooling generated by the second thermoelectric cooling device being configured to be applied to the face of the user with the user wearing the face mask, a second fan configured to cause a second air flow configured to dissipate the heat generated by the second thermoelectric cooling device, and a second noise attenuation system configured to attenuate noise caused by the second fan, the second noise attenuation system including at least one of a second flared acoustic waveguide, a second acoustic chamber, and a second tortuous path.

* * * * *